United States Patent [19]
Takenaka et al.

[11] 3,966,802
[45] June 29, 1976

[54] PROCESS FOR PREPARING ACRYLIC ACID AND OXIDATION CATALYST

[75] Inventors: Shigeo Takenaka; Hitoshi Shimizu; Masanobu Ogawa, all of Takasaki, Japan

[73] Assignee: Nippon Kayaku Kabushiki Kaisha, Tokyo, Japan

[22] Filed: Apr. 19, 1974

[21] Appl. No.: 462,310

Related U.S. Application Data

[62] Division of Ser. No. 336,058, Feb. 26, 1973, Pat. No. 3,857,796.

[30] Foreign Application Priority Data

Mar. 9, 1972 Japan.................................. 47-23603

[52] U.S. Cl............................. 260/530 N; 252/458; 252/467; 260/533 N
[51] Int. Cl.$^2$......................................... C07C 51/26
[58] Field of Search..................... 260/530 N, 533 N

[56] References Cited
UNITED STATES PATENTS

| | | | |
|---|---|---|---|
| 3,567,773 | 3/1971 | Yamaguchi et al............. | 260/530 N |
| 3,574,729 | 4/1972 | Gasson............................ | 260/530 N |
| 3,725,472 | 4/1973 | Kawano et al.................. | 260/530 N |
| 3,766,265 | 10/1973 | Shiraishi et al................. | 260/530 N |
| 3,773,692 | 11/1973 | Hensel et al.................... | 260/530 N |
| 3,775,474 | 11/1973 | Ohara et al..................... | 260/530 N |
| 3,825,600 | 7/1974 | Ohara et al..................... | 260/533 N |

*Primary Examiner*—Lorraine A. Weinberger
*Assistant Examiner*—P. J. Killos
*Attorney, Agent, or Firm*—Russell & Nields

[57] ABSTRACT

The present invention relates to a process for preparing acrylic acid by oxidizing acrolein and to an oxidation catalyst.

More particularly, the present invention relates to a catalyst and a process for preparing acrylic acid by oxidizing acrolein or a mixed acrolein gas obtained by vapor phase oxidation of propylene with molecular oxygen in the presence of an oxidation catalyst of the empirical formula:

$$Mo_aV_bT_cA_dO_e$$

wherein Mo, V and O represent molybdenum, vanadium and oxygen, respectively, T represents tungsten or antimony, A represents an alkali metal, and a, b, c, d and e represent number of atoms of Mo, V, T, A and O, respectively, and when a is 12, b is 0.5 to 6, c is 0 to 6, d is 0.01 to 1.5, preferably, 0.15 to 1.2 and e is naturally determined by the valence requirements of the other elements present.

5 Claims, No Drawings

PROCESS FOR PREPARING ACRYLIC ACID AND OXIDATION CATALYST

This is a division of application, Ser. No. 336,058 filed Feb. 26, 1973, now U.S. Pat. No. 3,857,796.

BACKGROUND OF THE INVENTION

Acrolein may be obtained by oxidizing propylene. In the preparation of acrylic acid by vapor phase catalytic oxidation of propylene, there have been the following three manners of carrying out the reaction:

1. One-step oxidation process wherein propylene is oxidized directly into acrylic acid in the presence of a catalyst.
2. Two-step process wherein acrolein is mainly prepared in the first oxidation step, acrolein is then separated from by-products such as acrylic acid and acrolein is oxidized in the second oxidation step.
3. A process wherein acrolein is mainly prepared in the first oxidation step and oxidized in the second oxidation step without separating acrolein from by-products or off gas (hereinafter this process will be referred to as the continuous process).

The present invention can be applied to either process (2) or (3). Particularly, if the present invention is applied to the continuous process, the merit that the yield of by-produced propionic acid can be reduced while the high yield of acrylic acid is kept can be obtained positively. Though acrylic acid obtained by vapor phase catalytic oxidation of propylene contains a small amount of propionic acid, separation of propionic acid therefrom is quite difficult by either a physical process such as distillation or by a chemical treatment, since they have nearly the same physical properties (such as boiling point) because the molecular weight of propionic acid is very close to that of acrylic acid, and since their chemical properties are very close to each other because their chemical structures are not so different from each other.

Further, the presence of propionic acid or an ester thereof which cannot be polymerized exerts a great influence upon the quality of acrylic acid or an ester thereof.

After investigations of reducing the by-production of propionic acid in the oxidation step, the inventors have confirmed that propylene unreacted in the first oxidation step and contained in the off gas is catalytically oxidized into propionic acid in the second oxidation step on a catalyst mainly comprising molybdenum and vanadium. Further a very small amount of propylene is converted into propionaldehyde in the first oxidation step and the propionaldehyde is converted into propionic acid in the second oxidation step.

Molybdenum-vanadium catalysts used for the preparation of acrylic acid from acrolein have been previously described in Japanese Pat. Publication Nos. 1775/1966, 1662/1967, 12129/1969, 12886/1969 and 26287/1969, etc. Those molybdenum-vanadium catalysts for the oxidation of acrolein have a poor activity for propylene at a reaction temperature suitable for the oxidation of acrolein. For example, under conditions for oxidizing more than 90% of acrolein, about 10% of propylene is oxidized.

The propylene, though in a small amount, is converted partially into propionic acid.

Thus, in case acrylic acid is to be prepared from propylene by the continuous process, if 100% of propylene is oxidized in the first oxidation step, propionic acid prepared will be in only a very small amount. However, 100% conversion of propylene causes a great reduction in selectivity to acrolein. Therefore, for preventing reduction in single pass yield of acrolein, conversion of propylene must be controlled to about 95 – 97%. Consequestly, 3 – 5% of propylene is introduced in the second oxidation step in this case.

DETAILED DESCRIPTION

The inventors considered whether the catalyst mainly comprising molybdenum and vanadium for the second oxidation step could be inactivated against propylene, keeping activity thereof against acrolein, by partial poisoning of the catalyst. If active points of the catalyst against acrolein and propylene are the same, this technique is impossible but if the points are different, this technique may be possible. On the basis of this consideration, the inventors have made experiments by using various poisons and found that the purpose can be attained by the addition of a small amount of an alkali metal.

Among the alkali metals, sodium is the most effective. Other alkali metals, that is potassium, lithium, rubidium and cesium, are effective too. If amount of the alkali metal is too large, the activity against acrolein is also lost and, on the other hand, if the amount is too small, the effects of poisoning activity against propylene is reduced. The catalyst of the present invention and the same catalyst but containing no alkali metal component were prepared in the same manner and they were used for the reaction of the same gas from the first oxidation step under the same conditions. In the presence of the catalyst of the present invention, propionic acid content was 550 ppm (mole) based on acrylic acid, while in the presence of the catalyst containing no alkali metal component, propionic acid content was 1300 ppm. Thus, by using the catalyst of the present invention, propionic acid content was reduced remarkably, while no great difference was observed in yield of acrylic acid (a little over 70 molar % based on propylene in both cases).

The catalyst of the present invention is prepared by known method, for example, by mixing a water-soluble molybdate such as ammonium molybdate, a water-soluble vanadate such as ammonium vanadate, a water-soluble salt of an alkali metal such as a sodium nitrate and, optionally, tungsten or antimony compound all in the form of aqueous solution or powder, adding if necessary, a suitable carrier such as Aerosil (finely powdered silica gel; a trade name of Degussa), evaporating the mixture to dryness, pulverizing the resulting cake into pieces having a suitable size and calcining them at a temperature of from 300° to 500°C, preferably from 350° to 450°C, in the presence of oxygen.

The starting materials used to prepare the catalyst such as molybdate is not restricted to the above mentioned compound.

Any starting material which can form the metal oxide or complex metal oxide with other metal after calcination treatment is useful.

Suitable carrier include silica, silicon carbide, alumina, diatomaceous earth, titanium oxide, etc. The catalyst is used in the form of granules or after shaping into tablets in a fixed bed or it may be used in the form of small particles in a fluidized bed or moving bed.

When the continuous process is adopted, a catalyst used in the first oxidation step may be any catalyst which oxidizes propylene into mainly acrolein.

In the first oxidation step, propylene is introduced together with air or mixed oxygen gas. If necessary, steam may also be introduced therein. The gas mixture sent from the first oxidation step to the second oxidation step comprises acrolein produced in the first oxidation step, unreacted propylene, oxygen, nitrogen, by-produced acrylic acid, acetic acid, carbon monoxide, carbon dioxide and steam.

The gas mixture is passed on the catalyst of the second oxidation step and the contact time is usually from 0.5 to 10 seconds (NTP). The catalytic oxidation process of the second oxidation step can be carried out at a temperature of from 250° to 350°C and at a pressure of from 0.5 to 10 atmospheres.

The mol ratios of ingredients in the gaseous feed mixture to the second oxidation step preferably are from 0.5 to 5 mols of oxygen and from 1 to 20 mols of steam per mol of acrolein. The process of the present invention is further illustrated by the following examples. In the present specification, the following definitions are employed.

Single pass yield of acrylic acid (%) =

$$\frac{\text{Mols of acrylic acid obtained}}{\text{Mols of propylene fed}} \times 100$$

Propionic acid content (ppm) =

$$\frac{\text{Mols of propionic acid obtained}}{\text{Mols of acrylic acid obtained}} \times 10^6$$

EXAMPLE 1

Catalyst of the first oxidation step is prepared by a method described in Example 1 of Japanese Pat. Publication No. 6245/1969. The resulting catalyst has the following general composition:

$Ni_{4.5}Co_4Fe_1Bi_1P_{0.08}Mo_{12}O_{52}$ 140 ml of the catalyst are placed in a stainless steel reaction tube of 20 mm inside diameter. The reaction tube is immersed in a 330°C of molten potassium nitrate bath and a gas mixture comprising propylene, air and steam in molar ratio of 1 : 12 : 6 is introduced therein, the contact time being 6 seconds (NTP).

95.0 % of propylene introduced in the first oxidation step has been reacted and the remainder 5 % is contained as unreacted propylene in the gas exhausted from the first oxidation step. 83 % of the reacted propylene is converted into acrolein and 6 % is converted into by-produced acrylic acid. The rest comprises mainly carbon dioxide and carbon monoxide and a small quantity of acetic acid is also contained therein. The gas exhausted from the first oxidation step comprising these gases, residual oxygen, nitrogen which does not participate in the reaction and steam is directly introduced in the second oxidation step.

A catalyst used in the second oxidation step is prepared in the following manner.

66.1 g of ammonium paramolybdate, 1.33 g of sodium nitrate and 10.9 g of ammonium methavanadate all dissolved in distilled water are mixed together. Further, 40 g of Aerosil in which $SiO_2$ content is 21 % are added thereto as carrier. The whole is heated under stirring and evaporated to dryness. Then, the produced cake is pulverized to 5 –20 mesh size and calcined at 400°C in air stream for 4 hours.

Composition of the catalyst thus obtained is represented by the formula:

$Mo_{12}V_3Na_{0.5}O_{43}$ (carrier $SiO_2$).

177 ml of the catalyst are placed in a stainless steel tube of 20 mm inside diameter immersed in a molten potassium nitrate bath, into which the gas containing acrolein from the first oxidation step is introduced. Temperature of the bath is regulated to 270°C.

Single pass yield of the acrylic acid is 71.0 %. Unreacted propylene is 4.8 % and by-produced acrolein is 3 %, the remainder being composed mainly of carbon dioxide, carbon monoxide and acetic acid.

Propionic acid content is 550 ppm.

COMPARATIVE EXAMPLE 1

The first oxidation step is carried out in the same manner as in Example 1 with respect to the apparatus, catalytic reaction conditions, etc. The gas exhausted from the first oxidation step is introduced in the second oxidation step. The second oxidation step is the same as in Example 1 except that the same catalyst as in the second oxidation step of Example 1 but containing no Na [general composition : $Mo_{12}V_3O_{43}$ (carrier $SiO_2$)] is used.

Yield of the acrylic acid is 72.2 %, unreacted propylene is 4.5 % and by-produced acrolein is 3 %.

Propionic acid content is 1300 ppm.

EXAMPLES 2 – 6

The procedures described in Example 1 are repeated except that the alkali metal content and/or kind of alkali it is changed. The results are shown in Table 1.

Table 1

| Ex. | Catalyst composition | Reaction bath temperature (°C) | Single pass yield of acrylic acid (%) | Propionic acid content (ppm) |
|---|---|---|---|---|
| 2 | $Mo_{12}V_3Li_{0.5}O_{43}$ | 270 | 70.5 | 670 |
| 3 | $Mo_{12}V_3K_{0.5}O_{43}$ | 270 | 70.7 | 590 |
| 4 | $Mo_{12}V_3Na_{0.4}O_{43}$ | 270 | 71.0 | 600 |
| 5 | $Mo_{12}V_3Na_{0.25}O_{43}$ | 270 | 71.2 | 880 |
| 6 | $Mo_{12}V_3Na_{0.1}O_{43}$ | 270 | 66.5 | 500 |
| 7 | $Mo_{12}V_3Rb_{0.5}O_{43}$ | 270 | 69.5 | 680 |
| 8 | $Mo_{12}V_3Cs_{0.5}O_{43}$ | 270 | 69.0 | 690 |

EXAMPLE 9

The first oxidation step is carried out in the same procedure as in Example 1. A catalyst prepared as follows is used in the second oxidation step. 66.1 g of ammonium paramolybdate, 10.9 g of ammonium methavanadate, 9.5 g of ammonium paratungstate and 1.3 g of sodium nitrate all dissolved in distilled water are mixed together and the mixture is further mixed with 40 g of Aerosil. The mixture is evaporated to dryness under stirring. Then, the produced cake is pulverized into 5 – 20 mesh size and calcined at 400°C for 4 hours.

Composition of the catalyst thus obtained is represented by the formula:

$Mo_{12}V_{2.5}W_1Na_{0.5}O_{47}$ (carrier $SiO_2$)

This catalyst is used as the oxidation catalyst in the second oxidation step. The same reaction conditions as in Example 1 are employed. Single pass yield of acrylic acid is 73.3 %. Propionic acid content is 570 ppm.

COMPARATIVE EXAMPLE 2

The procedure described in Example 7 are repeated except that the catalyst having the following composition is used in the second oxidation step.

$Mo_{12}V_3W_{1.2}O_{47}$ (carrier $SiO_2$)

Single pass yield of acrylic acid is 75.2 %. Propionic acid content is 1300 ppm.

EXAMPLE 10

The first oxidation step is carried out in the same procedure as in Example 1. A catalyst prepared as follows is used in the second oxidation step. 66.1 g of ammonium paramolybdate, 10.9 g of ammonium methavanadate and 1.3 g of sodium nitrate all dissolved in distilled water are mixed together and the mixture is further mixed with 14.2 g of antimony trioxide powder and 40 g of Aerosil. Then the mixture is heated under stirring and evaporated to dryness. Thus obtained cake is pulverized to 5 –20 mesh size and calcined at 400°C for 4 hours. Composition of the catalyst thus obtained is represented by the formula:

$Mo_{12}V_3Sb_3Na_{0.5}O_{48}$ (carrier $SiO_2$)

The catalyst is used in the second oxidation step in the same manner as in Example 1. The same reaction conditions as in Example 1 are employed.

Single pass yield of acrylic acid is 72.0 %. Propionic acid content of resulting acrylic acid is 570 ppm.

COMPARATIVE EXAMPLE 3

The procedure described in Example 8 are repeated except that the catalyst having the following composition is used in the second oxidation step.

$Mo_{12}V_3Sb_3O_{48}$ (carrier $SiO_2$)

Single pass yield of acrylic acid is 73.1 %. Propionic acid content is 1300 ppm.

EXAMPLES 11 - 21

The first oxidation step is carried out in the same manner as in Example 1. Catalyst shown in Table 2 prepared in the same manner as in Example 7 or Example 8 were used in the second oxidation step.

Reaction conditions, except for reaction bath temperature, and reaction apparatus are the same as in Example 1.

The results are shown in Table 2.

Table 2

| Example | Catalyst composition | Reaction bath temperature (°C) | Single pass yield of acrylic acid (%) | Propionic acid content (ppm) |
|---|---|---|---|---|
| 11 | $Mo_{12}V_1W_{0.5}Na_1O_{40}$ | 270 | 70.2 | 520 |
| 12 | $Mo_{12}V_{1.5}W_{0.5}K_{0.8}O_{41}$ | 280 | 72.1 | 540 |
| 13 | $Mo_{12}V_3W_1Na_{0.5}O_{46}$ | 270 | 72.8 | 560 |
| 14 | $Mo_{12}V_5W_2Li_1O_{55}$ | 270 | 71.9 | 610 |
| 15 | $Mo_{12}V_6W_{4.5}Li_{0.2}O_{64.5}$ | 280 | 69.8 | 690 |
| 16 | $Mo_{12}V_6Sb_5K_{0.2}O_{66.0}$ | 270 | 70.1 | 600 |
| 17 | $Mo_{12}V_2Sb_{0.5}Na_{0.5}O_{43}$ | 270 | 71.9 | 590 |
| 18 | $Mo_{12}V_{0.5}W_{0.5}Na_1O_{39}$ | 280 | 68.0 | 530 |
| 19 | $Mo_{12}V_4Sb_6Li_{0.5}O_{55}$ | 280 | 68.5 | 580 |
| 20 | $Mo_{12}V_3Sb_1Na_{0.01}O_{45}$ | 270 | 67.5 | 900 |
| 21 | $Mo_{12}V_{2.5}W_{0.5}Na_{1.5}O_{45}$ (carrier $SiO_2$) | 270 | 60.0 | 300 |

We claim:
1. In the continuous process for preparing acrylic acid by vapor phase oxidation of propylene wherein acrolein is mainly prepared in the first oxidation step and oxidized in the second oxidation step without separating acrolein from by-products or off gas, the improvement which comprises carrying out said second oxidation step with molecular oxygen in the presence of an oxidation catalyst of the empirical formula:

$Mo_aV_bT_cA_dO_e$ wherein Mo, V and O represent molybdenum, vanadium and oxygen, respectively, T represents tungsten or antimony, A represents an alkali metal, and a, b, c, d and e represent number of atoms of Mo, V, T, A and O, respectively, and when a is 12, b is 0.5 to 6, c is 0 to 6, d is 0.01 to 1.5 and e is a number naturally determined by the valence requirements of the other elements present, said catalyst being prepared by mixing a water-soluble molybdate, a water-soluble vanadate, a water-soluble salt of an alkali metal and, optionally, tungsten or antimony compound all in the form of aqueous solution or powder, adding, if necessary, a suitable carrier, evaporating the mixture to dryness and calcining the dried mixture at a temperature of from 300° to 500°C.

2. The process of claim 1, wherein a is 12, b is 0.5 to 6, c is 0 to 6, d is 0.15 to 1.2.

3. The process of claim 1, wherein the catalyst is incorporated on a silica carrier.

4. The process of claim 1, wherein the reaction is carried out at a temperature of from 250° to 350°C.

5. The process of claim 1, wherein the molar ratio of oxygen, steam and acrolein is 0.5 – 5 : 1 – 20 : 1.

* * * * *